(12) United States Patent
Kohl

(10) Patent No.: US 10,113,007 B2
(45) Date of Patent: *Oct. 30, 2018

(54) ADVANCED COOK TECHNOLOGY

(71) Applicant: ICM, Inc., Colwich, KS (US)

(72) Inventor: Scott D Kohl, Wichita, KS (US)

(73) Assignee: ICM, Inc., Colwich, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/073,046

(22) Filed: Nov. 6, 2013

(65) Prior Publication Data

US 2014/0127772 A1     May 8, 2014

Related U.S. Application Data

(60) Provisional application No. 61/723,195, filed on Nov. 6, 2012.

(51) Int. Cl.

| | |
|---|---|
| *C12P 7/10* | (2006.01) |
| *C08B 30/02* | (2006.01) |
| *C08B 30/04* | (2006.01) |
| *C08B 30/12* | (2006.01) |
| *C08B 30/18* | (2006.01) |
| *C08H 8/00* | (2010.01) |
| *C12P 19/02* | (2006.01) |
| *C12P 19/14* | (2006.01) |

(52) U.S. Cl.
CPC ............ *C08B 30/02* (2013.01); *C08B 30/042* (2013.01); *C08B 30/12* (2013.01); *C08B 30/18* (2013.01); *C08H 8/00* (2013.01); *C12P 19/02* (2013.01); *C12P 19/14* (2013.01); *Y02E 50/16* (2013.01)

(58) Field of Classification Search
CPC ................. B01D 1/00; B01D 17/0217; C10G 2300/1014; C10G 2300/1018; C10G 2300/44; C10L 1/026; C10L 1/1802; C11B 13/00; C11B 3/08; C11B 3/16; C12F 3/10; Y02E 50/10; Y02E 50/30; Y02E 50/16; Y02P 30/20; C08B 30/02; C08B 30/042; C08B 30/12; C08B 30/18; C08H 8/00; C12P 19/02; C12P 19/14
See application file for complete search history.

(56) References Cited

U.S. PATENT DOCUMENTS

| | | |
|---|---|---|
| 4,311,714 A | 1/1982 | Goering et al. |
| 5,559,031 A | 9/1996 | Zinnamosca et al. |
| 7,452,425 B1 | 11/2008 | Langhauser |
| 2006/0006116 A1* | 1/2006 | Scheimann et al. .......... 210/728 |
| 2007/0254089 A1* | 11/2007 | Hickey et al. ................ 426/624 |
| 2009/0181153 A1 | 7/2009 | Bendorf et al. |
| 2009/0259018 A1* | 10/2009 | Barrows et al. .............. 530/300 |
| 2012/0244590 A1* | 9/2012 | Lee .............................. 435/161 |
| 2014/0011258 A1* | 1/2014 | Medoff .................... C12P 19/14 435/209 |
| 2014/0024093 A1* | 1/2014 | Blackbourn ............. D21C 3/20 435/158 |

FOREIGN PATENT DOCUMENTS

| | | |
|---|---|---|
| WO | WO-9103543 A1 | 3/1991 |
| WO | WO-2006052787 A2 | 5/2006 |
| WO | WO-2014075568 A1 | 5/2014 |

OTHER PUBLICATIONS

Research Disclosures Document 185019, CPC International, Inc. (1979) 185(9): 481.*
Research Disclosures Document 217038, Anonymous (1982) 217(5): 190.*
Sims et al. (2008) From $1^{st}$ to $2^{nd}$ Generation Biofuel Technologies: An overview of current industry and RD&D activities. IEA Bioenergy. pp. 1-120.*
Canadian Application No. 2,832,446, Examination Report dated Feb. 27, 2014, 4 pgs.
Canadian Application No. 2,832,446, Response filed May 20, 2014 to Examination Report dated Feb. 27, 2014, 40 pgs.
Canadian Application No. 2,832,446, Notice of Allowance dated Jun. 30, 2014, 1 pg.
"International Application Serial No. PCT/US2013/068670, International Search Report dated Feb. 5, 2014", 3 pgs.
"International Application Serial No. PCT/US2013/068670, Written Opinion dated Feb. 5, 2014", 6 pgs.
International Application Serial No. PCT/US2013/068670, International Preliminary Report on Patentability dated May 21, 2015, 8 pgs.

* cited by examiner

*Primary Examiner* — Lisa J Hobbs

(74) *Attorney, Agent, or Firm* — Schwegman Lundberg & Woessner, P.A.

(57) ABSTRACT

This disclosure describes providing techniques to treat large-size solids obtained from a slurry or a mash in dextrin production process as can be used in an alcohol production process. This disclosure describes a process for separating a large-particles stream from a liquid stream containing small particles of a process stream using a first mechanical separation device. The process further includes adding water to the large-particles stream to create a lower-solids stream in a cook tank. In an embodiment, the process may grind the large particles from the large-particles stream. In another embodiment, the process may adjust conditions (temperature, pH, processing aids addition) of the lower-solids stream in the cook tank and incubating for a predetermined amount of time. The process further includes separating components from the lower-solids stream by using a second mechanical separation device.

9 Claims, 8 Drawing Sheets

ADVANCED COOK TECHNOLOGY

CROSS REFERENCE TO RELATED APPLICATION

This application claims priority to U.S. Provisional Application No. 61/723,195, filed on Nov. 6, 2012, the contents of which is hereby incorporated by reference in its entirety.

TECHNICAL FIELD

The subject matter of this disclosure relates to increasing an amount of product produced per bushel of grain. In particular, the subject matter is directed to separating large particles in a process stream and treating the large particles to increase starch conversion and to recover more oil and protein per bushel of grain.

BACKGROUND

Typically, a dry grind process or a wet mill process may be used for producing alcohol, ethanol, butanol, and the like in a production facility. The dry grind process offers some advantages over the wet mill process. For instance, the dry grind process provides lower capital costs and lower operating costs than the wet mill process. However, the dry grind process tends to have problems in converting starch to ethanol. As a result, a portion of the starch passes through the dry grind process unconverted and exits the process as Distillers Grains, Distillers Wet Grains, Distillers Dried Grains with Solubles (DDGS), or Condensed Distillers Solubles (CDS).

The wet mill process is designed to better separate components of the grain, in which the components may be efficiently recovered and purified. The wet mill process produces more high-valued products, such as food products, alcohol, gluten meal, gluten feed, starch, oil, and syrup. However, wet mills cost substantially more to build and have higher operating costs than dry grind mills. Wet mills are also typically much larger in size and have a larger footprint than the dry grind mills.

There has been a variety of methods attempted to convert starch to alcohol to increase yield in the dry grind process. For instance, one method uses high temperature to cook components separated from feedstock. The high temperature being used is in excess of 120° C. (248° F. or 393 K). Typically, many processes heat the components to less than 100° C. (212° F. or 373 K). Unfortunately, a problem occurs when using the higher temperature in excess of 120° C. (248° F. or 393 K), which results in extra energy costs for the production facility and tends to damage quality of the DDGS.

Another method attempted a raw starch hydrolysis system. This system uses a combination of a very fine grind along with large amounts of specialized enzymes to convert the starch. This process makes great efforts to increase the surface area in order to maximize starch conversion. The process is conducted at low temperature, generally beneath the gelatinization range of the starch material. However, problems exist that include the fine grind creating excess fine particles, which needs additional equipment to remove the excess fines and the low temperature allowing for bacterial contamination to occur. Also, another problem is that this method significantly increases the amount of capital costs and energy usage than a typical process. Furthermore, there are additional costs associated with the large amounts of specialized enzymes.

Another method attempted to create a fine grind in a dry grind process. The process grinds the grain very fine initially. One problem is the difficulty of getting good mixing of the freshly ground feedstock with hot mashing water. Dough balls tend to form due to the fines (i.e., ground material) not mixing well with the hot mashing water. Furthermore, back-end problems exist where the fines are difficult to remove from centrate water stream. This creates centrate evaporation issues and a higher viscosity syrup. Thus, problems include: the dough balls create processing problems, the fines create removal problems, and the increase in backset solids reduces the amount of feedstock able to be put into the cooking process.

Accordingly, there is a need for converting starch to alcohol in a more cost efficient manner without significantly affecting quality of the product or co-products, without increasing water, energy, or capital costs while improving oil recovery and yield.

SUMMARY

The subject matter relates to improving milling techniques to increase product yield and to recover more co-products in an alcohol production facility.

This disclosure describes techniques to treat large particles obtained from a process stream in the alcohol production process. In an embodiment, a process separates the components of the process stream by using a first mechanical separation step. The process produces a first large-particles stream and a first liquid stream containing small particles and dissolved components. The process sends the first large-particles stream to a tank and adds water, which creates a dilute lower-solids stream. The process heats the dilute lower-solids stream in the tank at a temperature lower than about 150° C. (302° F. or 423 K) for a predetermined amount of time.

In another embodiment, a process separates a first large-particles stream from a first liquid stream containing small particles and dissolved components of a process stream by using a first mechanical separation step. The process may send a portion of the first large-particles stream through a mechanical milling device to grind the large-size particles. The process adds water to to create a lower-solids stream in a tank and heats the lower-solids streams in the tank for a predetermined amount of time. Then, the process removes extra water from the lower-solids stream by using a second mechanical separation step that further separates a second large-particles stream from a second liquid stream containing small particles of the lower-solids stream.

In yet another embodiment, a process separates a large-particles stream from a liquid stream containing small particles and dissolved components of a process stream using a first mechanical separation step. The method further includes adding water to the large-particles stream to create a lower-solids stream in a cook tank and adjusting conditions (e.g., temperature, pH, or processing aids addition) of the lower-solids stream in the cook tank and incubating for a predetermined amount of time at a predetermined temperature. The process further includes removing extra water from the lower-solids stream by using a second mechanical separation step.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other aspects and advantages of the claimed subject matter will be apparent from the following Detailed Description of the embodiments and the accompanying figures.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The figures do not limit the claimed subject matter to specific embodiments described herein.

DETAILED DESCRIPTION

Overview

Figure 1:
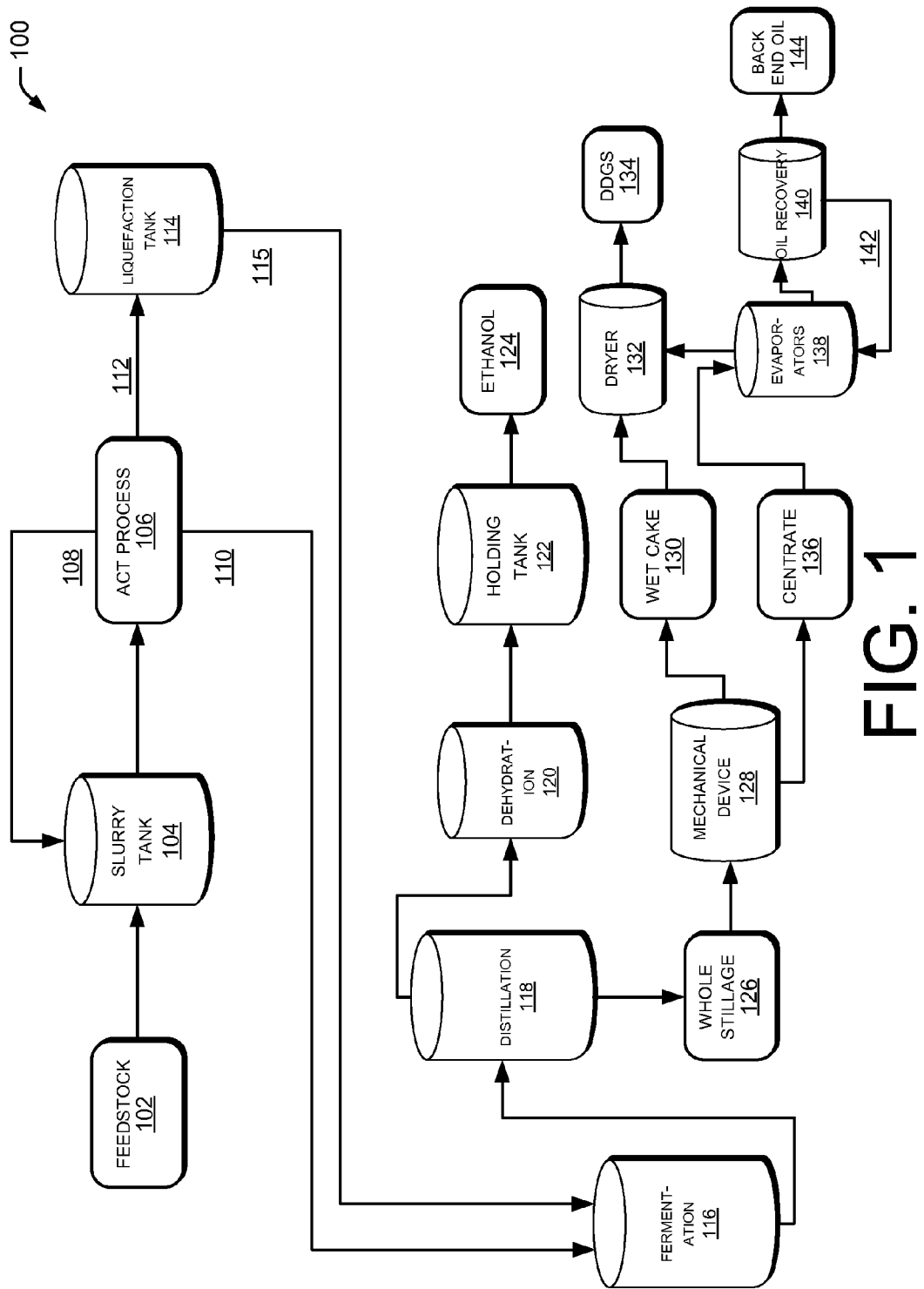
FIG. 1 illustrates an example environment for treating the large-size solids obtained from slurry in an Advanced Cook Technology (ACT) process.

The Detailed Description explains embodiments of the subject matter and the various features and advantageous details more fully with reference to non-limiting embodiments and examples that are described and/or illustrated in the accompanying figures and detailed in the following attached description. Descriptions of well-known components and processing techniques may be omitted so as to not unnecessarily obscure the embodiments of the subject matter. The examples used herein are intended merely to facilitate an understanding of ways in which the subject matter may be practiced and to further enable those of skill in the art to practice the embodiments of the subject matter. Accordingly, the examples, the embodiments, and the figures herein should not be construed as limiting the scope of the subject matter, nor intended to identify key features of essential features of the claimed subject matter.

Typically, a dry grind process has difficulties in converting starch to ethanol. A common problem occurs when the dry solids (percent weight of non-water component in water-based liquefaction) content is elevated during the conversion of starch to dextrins and sugars. The elevated solids content tends to increase viscosity of the slurry and to decrease yield of starch to dextrins resulting in decreased ethanol production from the subsequent fermentation process. The increase in viscosity negatively affects the movement of the slurry in the process while the decrease in yield from the fermentation is attributed to the difficulty in hydrolyzing starch to dextrins. For instance, the increase in the solids content causes a decrease in an amount (concentration) of water activity available in the process. However, water is required for hydrolysis of starch to dextrins. Thus, the decrease in water activity decreases a rate of hydrolysis and the ability to get a completion of the hydrolysis.

This disclosure describes techniques to address the difficulties in converting starch to dextrins and ultimately starch to ethanol. For instance, the techniques describe an Advanced Cook Technology (ACT) process to improve the conversion of starch to alcohol. While the techniques are described using various phases and/or steps, the phases and/or steps are not order dependent and some phases or steps may be omitted in the various embodiments.

In a first embodiment, the ACT process initially separates or filters components of the feedstock in a process stream, heats, cools, or otherwise treats large-size particles from the separated streams, and further separates the large-size particles for processing. In the initial separating phase, the ACT process obtains the process stream in an alcohol production process and separates the components of a first large-size particles in the stream from a first liquids and the small-size particles in the stream by using a first mechanical separation device. The first large-size particles tend to contain unhydrolyzed starch. In the heating or cooking phase, the ACT process adds water to the first large-size particles stream to create a dilute, lower-solids stream, and heats this dilute lower-solids stream for a predetermined amount of time in a tank. This raises the water activity level for better starch to dextrin (sugar) conversion. In the second separating phase, the ACT process further separates a second large-size particles from a second liquids and small-size particles by using a second mechanical separation device. This removes the additional water that was added in the cooking phase and recovers starch and dextrin liberated from the suspended solids. The advantages include increasing the amount of starch converted to dextrins and sugars and creating conditions for better starch to sugar conversion, which improves the yield.

In another embodiment, the ACT process initially separates the components of the feedstock in a process stream in a first separation phase, grinds or mills the large-size particles from the separated streams in a grinding or milling phase, heats, cools, or otherwise treats the ground large-size particles from the separated streams in a cook phase, and further separates the large-size particles for processing in a second separation phase. This embodiment is similar to the first embodiment discussed above but includes the grinding or milling phase.

In the grinding or milling phase, the ACT process shears the large-size particles to break down the large-size particles in order to remove the starch, oil, and protein from fiber and germ by using a mechanical milling device. In the heating, cooking, or otherwise treatment phase, the ACT process adds water to the ground large-size particles to create a lower-solids stream, and heats this lower-solids stream for a predetermined amount of time in a tank. This raises the free water activity for better starch to sugar conversion. In the second separating phase, the ACT process further separates the large-size particles from the liquids and small-size particles by using a second mechanical separation device. The advantages for performing these phases in this embodiment are similar to the advantages discussed previously for the first embodiment along with the advantages of shearing to reduce the particle size and to remove the associations (bonds or strong interactions) between the fiber and germ with the starch, oil, and protein naturally found associated with the fiber and germ.

In yet another embodiment, the ACT process initially separates the components of the feedstock in a process stream, heats, cools, or otherwise treats the large-size particles from the separated streams, either adjusts temperature, adds enzymes or adjusts pH as needed, to the large-particles streams from the separated streams, and further separates the large-particles stream for processing. This embodiment is similar to the first embodiment discussed above but includes adjusting temperature, adding enzymes, or adjusting pH phases.

In yet another embodiment, the ACT process initially separates the components of the feedstock in a process stream, treats the large-size particles from the separated streams by adjusting pH, temperature or processing aids as needed, to the large-particles streams from the separated streams. The process may further include incubation and separation of the large-particles stream for additional processing. This embodiment is similar to the embodiment discussed above, but includes the adjusting pH, adjusting temperature, or processing aids along with the incubation phase.

The adding enzymes phase includes adding enzymes that include but is not limited to, alpha-amylases, proteases, gluco-amylases, pullulanases, as well as other hydrolytic enzymes to the large-particles stream after being heated or cooked in the tank. This phase further increases the conversion of starch to dextrin, which further improves yield of product. This additional enzyme phase increases the residence time. The longer residence time in combination with the lower suspended materials completes the starch to dextrin process more completely. Also, the additional enzymes being added to the lower solids may cause oil to leach from fine germ particles. The adjusting pH phase includes adding acids or bases to the large-particles stream. An optimum pH level depends on variables, such as the type of enzymes being used in the process. The advantages for performing these phases in this embodiment are similar to the advantages discussed previously for the first embodiment along with increasing the starch conversion and causing oil to leach from the fine germ particles.

In another embodiment, the ACT process initially separates the components of the feedstock in a process stream, grinds or mills the large-size particles from the separated streams, heats or cools the ground large-size particles from the separated streams, adds enzymes to the large-size particles from the separated streams, and further separates the large-size particles for processing. This embodiment is similar to the embodiments discussed above. The advantages for performing the phases in this embodiment are similar to the advantages discussed above.

Additional advantages of the ACT process include not creating a very fine grind that causes dough balls, and having reasonable capital costs associated with equipment. Furthermore, the ACT process avoids creating high fines for back-end recovery of a cold cook or a fine grind of a dry grain. The equipment used in the ACT process includes utilizing a minimal number of equipment at reasonable capital costs. Thus, there are many advantages to using the ACT process in the alcohol production facility.

While aspects of described techniques can be implemented in any number of different environments, and/or configurations, implementations are described in the context of the following example processes.

Illustrative Processes

FIGS. 1-8 include flow diagrams showing example processes of the ACT process. The processes may be performed using a combination of different systems and/or types of equipment. The equipment should not be construed as necessarily order dependent in their performance. Any number of the described environments, processes or types of equipment may be combined in any order to implement the method, or an alternate method. Moreover, it is also possible for one or more of the provided steps, phases, or pieces of equipment to be omitted.

FIG. 1 illustrates an example of an alcohol process 100 implementing a series of operations in a wet mill and/or a dry grind mill of a production facility. The process 100 in the alcohol production may operate in a continuous manner. In other implementations, the process 100 may operate in a batch process or a combination of batch and continuous process.

The process 100 may receive feedstock of a grain that includes but is not limited to, barley, wheat, oats, rye, triticale, sweet potatoes, cassava, corn, milo, sorghum grain, lignocellulosic biomass, and the like. Also, the feedstock may further include, grain fractions or by-products as produced by industry, such as hominy, wheat middlings, corn gluten feed, DDGS, and the like. The feedstock may include an individual type, a combined feedstock of two types, of multiple types, or any combination or blend of the above grains. The feedstock may include but is not limited to, one to five different types combined in various percentage ranges. The feedstock may be converted into different products and co-products that may include but is not limited to, germ to be extracted for oil, food grade protein meal for high protein animal feed, and starch-based and fermentation-based products such as ethanol, syrup, food, and industrial starch. The feedstock may be processed for other applications that include but are not limited to, producing chemicals for use in other applications, producing plastics, and the like.

For brevity purposes, the process 100 of using a single stream of feedstock will be described with reference to FIG. 1. As an example, corn may be used as a single feedstock. Corn may be broken down into its major components of endosperm, germ, bran coat, and tip cap. Each of these major components may be further broken down to their smaller components. The endosperm, the germ, the bran, and the tip cap each contains varying amounts of starch, protein, oil, fiber, ash, sugars, etc. For instance, the amounts of the components in corn may include, but are not limited to about 72% starch, about 8% protein, about 4% oil, about 9% fiber, about 1% ash, about 2% sugars, and others.

One skilled in the art understands that the inspecting and cleaning of the corn occurs initially. At 102, the process 100 initially grinds the feedstock 102 into a meal, a powder, or a flour. The grind feedstock 102 may occur by using hammer mills or roller mills. This grinding serves to break an outer coating of the corn kernel and increases a surface area to expose starch.

In an embodiment, the process 100 uses a hammer mill (not shown). The hammer mill is a cylindrical grinding chamber with a rotating drum, flat metal bars, and a screen. The screen size may be almost any size smaller than the whole grain kernel being processed, preferably $4/64$ to $12/64$ inch hole sizes. An example hammer mill may have screen openings that are sized $7/64$, or about 2.78 millimeters (mm) to create particles that are sized about 0.5 to about 2-3 mm.

In another embodiment, the process 100 uses a roller mill (not shown). The roller mill receives the feedstock 102, passes the feedstock 102 between two or more rolls or wheels, and crushes the feedstock in the process. One roll may be fixed in position while the other roll may be moved further or closer towards the stationary roll. The roll surfaces may be grooved to help in shearing and disintegration of the corn (or other starch containing feedstock). The rolls may be about 9 to about 12 inches (23 to 30.5 cm) in diameter, with a ratio of length to diameter that may be about 4:1. The particles may be sized about 0.5 to about 2-3 mm.

At slurry tank 104, the process 100 adds water and enzymes to the ground grain 102 to create a slurry in the slurry tank 104. In an example, the process 100 adds an enzyme, such as alpha-amylase. The alpha-amylase enzyme breaks the starch polymer into short sections, termed dextrins. The process 100 maintains a temperature between about 60° C. (140° F. or 333 K) to about 100° C. (212° F. or 373 K) in the slurry tank 104 to cause the starch to gelatinize and a residence time of about 30 to about 60 minutes to convert the insoluble starch in the slurry to soluble starch. The slurry may have suspended plus dissolved solids content of about 26 to about 44%, which includes starch, fiber, protein, and oil. Other components in the slurry tank 104 may include grit, salts, and the like as is commonly present on raw incoming grain from agricultural production as well as recycle waters that contain processing aids, such as acids, bases, salts, yeast, and enzymes. The process 100 adjusts the pH of the slurry to about 4.5 to 6.0 (depending on enzyme type) in the slurry tank 104.

In an embodiment, the slurry may be heated to further reduce viscosity of the ground grain. In some embodiments, a jet cooking process is included. In some embodiments, there may be two or more slurry tanks to be used for an additional residence time and a viscosity reduction.

For illustrative purposes in FIG. 1, the ACT process 106 is presented at a high level. Details of the ACT process 106 embodiments will be discussed later with reference to FIGS. 2-7. The ACT process 106 may be included with any alcohol process as part of the alcohol production facility or any type of process in a production facility. Specifically, the ACT process helps to increase the amount of product and co-products produced per bushel and to recover more oil and protein per bushel of grain.

The ACT process 106 obtains the process stream as the slurry from the slurry tank 104 to separate the large-size particles in the stream from the small-size particles and dissolved components in the stream. In other embodiments, the ACT process may obtain the process stream as the slurry from a second slurry tank, may obtain the process stream from a jet cooker, may obtain the process stream as mash from a first liquefaction tank, obtain the process stream as the mash from a second liquefaction tank, or obtain after a pretreatment process in a cellulosic production facility.

The ACT process 106 uses one or more mechanical separation devices to separate the larger-size particles in the stream (e.g. the suspended-solids stream) from the smaller-size particles in the stream (e.g. liquids stream with fine-suspended solids and dissolved components). These different streams are further processed and described in details with references to FIGS. 2-7.

After undergoing the different processes, there may be at least two to three streams exiting from the ACT process 106 as shown. These are examples which include, but are not limiting of the different streams exiting from the ACT process 106. At 108, another liquids and fine-suspended solids stream separated from the large-particles stream is sent back to the slurry tank 104. In other embodiments, the large-particles stream may be sent to the second slurry tank, the jet cooker, a first or a second liquefaction tanks, or hydrolysis tank. At 110, another large-particles stream may be combined with the liquids and fine-suspended solids stream, which are sent to a fermentation tank, bypassing the liquefaction tank 114. At 112, the large-particles stream may be filtered and sent to a liquefaction tank 114.

In an embodiment, the process 100 pumps the slurry to jet cookers (not shown) to cook the slurry. Jet cooking may occur at elevated temperatures and pressures. For example, jet cooking may be performed at a temperature of about 104° C. to about 150° C. (about 220 to about 302° F., about 377 to about 423 K) and at an absolute pressure of about 1.0 to about 6.0 kg/cm$^2$ (about 15 to 85 lbs/in$^2$) for about five minutes. Jet cooking is another method used to gelatinize the starch.

At liquefaction tank 114, the process 100 converts the slurry to mash in the liquefaction tank 114. The process 100 uses a temperature range of about 80 to about 150° C. (about 176 to 302° F., about 353 to about 423 K) to hydrolyze the gelatinized starch into maltodextrins and oligosaccharides to produce a liquefied mash. Here, the process 100 produces a mash stream, which has about 18 to about 45% total solids content. The mash may have suspended solids content that includes fiber, germ, grit, and the like. In embodiments, one or more liquefaction tanks may be used in the process 100.

The process 100 may add another enzyme, such as glucoamylase in the liquefaction tank 114 to break down the dextrins into simple sugars. Specifically, the glucoamylase enzyme breaks the short sections into individual glucose molecules. The process 100 may add the glucoamylase enzyme at about 60° C. (about 140° F. or about 333 K) before fermentation starts, known as saccharification or at start of a fermentation process. In an embodiment, the process 100 further adjusts the pH to about 5.0 or lower in the liquefaction tank 114. In another embodiment, saccharification and fermentation may also occur simultaneously. The process stream 115 travels from liquefaction tank 114 to fermenation 116.

At fermentation 116, the process 100 adds a microorganism to the mash for fermenting in a fermentation tank. The process 100 may use a common strain of microorganism, such as *Saccharomyces cerevisae* to convert the simple sugars (i.e., maltose and glucose) into alcohol with solids and liquids, $CO_2$, and heat. The process 100 may use a residence time in the fermentation tank 116 as long as about 50 to about 80 hours. However, variables such as a microorganism strain being used, a rate of enzyme addition, a temperature for fermentation, a targeted alcohol concentration, and the like may affect fermentation time. In embodiments, one or more fermentation tanks may be used in the process 100.

The process 100 creates the alcohol, solids, and liquids through fermentation 116 in the fermentation tank. Once completed, the mash is commonly referred to as beer, which may contain about 10 to about 20% alcohol, plus soluble and insoluble solids from the grain components, microorganism metabolites, and microorganism bodies. The microorganism may be recycled in a microorganism recycling step, which is an option.

Turning to distillation 118, the process 100 distills the beer to separate the alcohol from the solids and the liquids by using a distillation process, which may include one or more distillation columns or evaporators. The process 100 pumps the beer through a distillation process=, which is boiled to vaporize the alcohol. The process 100 condenses the alcohol vapor in the distillation process where vapor alcohol exits through a top portion of the distillation process at about 88 to about 95% purity, which is about 190 proof, and is subsequently condensed to a liquid. In embodiments, one to eight distillation columns may be used in the distillation process. In embodiments, the distillation columns or evaporators may be in series or in parallel. There may be multiple effect evaporators, such as any number of evaporators, from one to about eight evaporators. Some process streams may go through a first effect evaporator(s), which operate at high temperatures, and second effect evaporator(s), which operate at lower temperatures. Factors affecting distillation 118 include column size, energy flux, product flow rate, and ethanol concentration.

At dehydration 120, the process 100 removes moisture from the 190 proof alcohol by going through a molecular sieve process. The molecular sieve process may include one or more dehydration column(s) packed with molecular sieve media to yield a product of nearly 100% alcohol, which is 200 proof.

At holding tank 122, the process 100 adds a denaturant to the alcohol prior to or in the holding tank 122. Thus, the alcohol is not meant for drinking but is to be used for motor fuel purposes. At 124, an example product that may be produced is ethanol, to be used as fuel or fuel additive for motor fuel purposes.

At whole stillage 126, the water-rich product remaining from distillation 118 is commonly referred to as "whole stillage." The components in the whole stillage 126 may include suspended grain solids, dissolved materials, and water. For instance, the components also include oil, protein, fiber, and minerals. Whole stillage 126 falls to the bottom of the distillation 118 and passes through a mechanical device 128.

The mechanical device 128 separates the whole stillage 126 to produce wet cake 130 (i.e., insoluble solids) and centrate 136 (i.e., liquids). The mechanical device 128 may include but is not limited to, a centrifuge, a decanter, or any other type of separation device.

The wet cake 130, primarily solids, may be referred to as Distillers Wet Grains (DWG). Some of the wet cake 130 is transferred to one or more dryer(s) 132 to remove liquids. This drying produces Distillers Dried Grains (DDG), which may be stored in tanks to be used as livestock feed (not shown). Some syrup from the thin stillage may be dried with the DWG to produce Distillers Dried Grains with Solubles (DDGS) 134.

Returning to centrate 136, the composition of the centrate 136 (also thin stillage) is mostly liquids left over from whole stillage 126. The process 100 sends the centrate 136 to the evaporators 138 to boil away the water from the thin stillage, leaving a thick syrup (i.e., 25 to 40% dry solids) which contains soluble (dissolved), fine suspended (generally less than 50 μm) and buoyant suspended solids from fermentation. The process 100 sends the thick syrup from the evaporators 138 to the dryer 132 drying the wet cake 130 (i.e., WDG) to produce DDGS 134.

In another embodiment, the process 100 may send the liquids to a device for oil recovery 140, which removes oil from the syrup to recover oil. The process 100 may send materials 142 from the oil recovery 140 back to the evaporators 138. As a result, the process 100 produces a product of back-end oil 144.

Illustrative Advanced Cook Technology Embodiments

Figure 2:
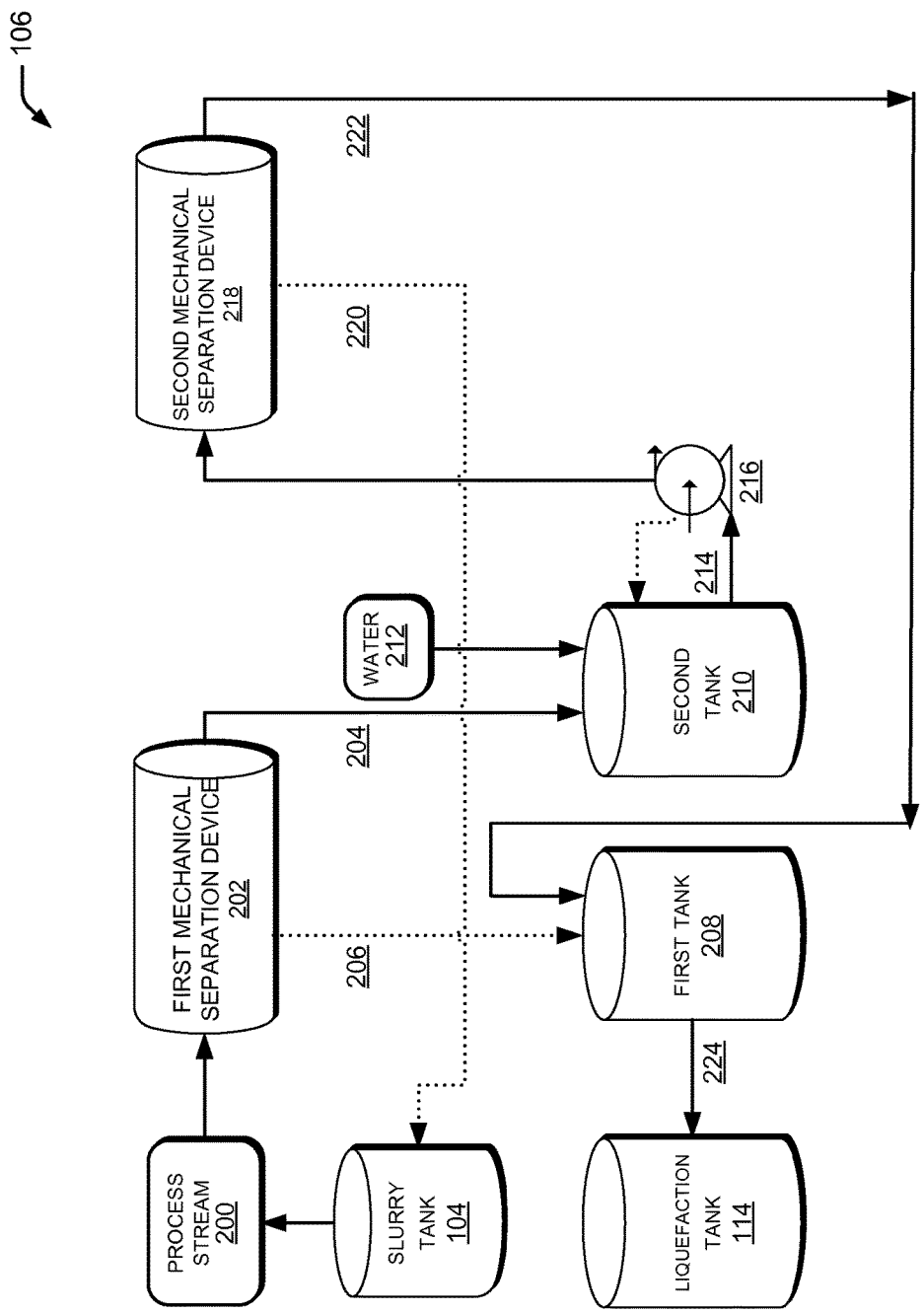
FIG. 2 illustrates an example embodiment of the ACT process with separation steps.

FIG. 2 illustrates an example of the ACT process 106. For illustrative purposes, the ACT process 106 obtains a process stream 200 as the slurry from a slurry tank 104. As mentioned, other embodiments include but are not limited to, the ACT process 106 obtaining the process stream from a second slurry tank, from a jet cooker, from a first liquefaction tank, from a second liquefaction tank, from a pretreatment tank, from a hydrolysis tank, and the like. For discussion purposes, the different types of streams are identified by numerals to help keep track of the streams. The numerals are not meant to indicate any type of order. In some embodiments, some of the streams may be omitted.

The ACT process 106 includes the phases of initially separating the components of the feedstock in the process stream, heating or cooking the large-size particles from the separated streams with water added, and further separating the large-size particles for processing. Details of each of the phases will be discussed below with reference to FIG. 2. For illustrative purposes, the liquids stream and fine suspended solids will be illustrated with dotted lines.

The ACT process 106 separates components of the feedstock in the process stream 200, such as separating the solids stream from the liquids stream by using a first mechanical separation device 202. This separation produces a large-suspended solids stream 204 and a liquids and fine-suspended solids stream 206. The large-suspended solids stream 204 and the liquids and fine-suspended solids stream 206 each contain suspended solid particles, which may be separated from the process stream 200. For instance, the large-suspended solids stream 204 has a higher concentration, which may affect the ACT process 106 in adjusting the conditions for this stream. Terms, such as the "large-suspended solids stream" and the "large particles" may be used interchangeably to indicate the solids that are suspended in water. The large-suspended solids stream contains larger sized particles than the fine-suspended solids that are suspended in water with smaller sized particles and dissolved components.

The first mechanical separation device 202 includes at least one of a paddle machine, a washing paddle machine, a filtration centrifuge, a pressure screen, a gravity DSM screen, a vibration screen, and the like to separate the solids from the liquids. In an embodiment, the first mechanical separation device 202 is a paddle machine having at least four rotating paddles with a stationary drum and an outer wall configured as a screen. In other embodiments, the paddle machine may include at least two rotating paddles or more, up to 20 rotating paddles. In embodiments, the paddle machine may be about 24 inches in length, about 36 inches in length, or about 52 inches in length.

The first mechanical separation device 202, pushes the process stream 200 against a screen where the liquids and small particles (i.e., starch, gluten, protein, salt, and the like) pass through the screen and are sent to a first tank 208. Paddles may rotate to move the process stream 200 toward the screen. The screen has openings sized to allow water, starch, and smaller sized particles to flow through the screen but will not allow the larger particles, such as fiber to flow through. For instance, the screen sizes may range from about 28 microns to about 600 microns. Smaller screen openings increase the alcohol yield while providing an increase in concentration of protein and oil recovered through the screens. In an embodiment, the liquids and fine-suspended solids stream 206 may include small-suspended particles, which may be up to about two times the size of the screen opening used. Meanwhile, the large-suspended solids stream 204 may include large-suspended particles mostly that are approximately the size of the screen openings or larger. This liquids and fine-suspended solids stream 206 will be discussed in more details later.

The steams contain various components. For instance, the liquids and fine-suspended solids stream 206 may include starch that has been removed from the fiber, as well as dissolved components. However, the large-suspended solids stream 204 may still contain unhydrolyzed starch, the gluten food grade protein along with the fiber, and the oil with the germ particles. Thus, the ACT process 106 may separate starch, oil, and protein from the fiber and the germ particles through a series of mechanical separation devices.

For instance, the ACT process 106 may include but is not limited to, one to about ten series of separation steps. Embodiments may include but are not limited to a series of counter-flow washing or a series of current-flow washing. An example of the ACT process with counter-flow washing will be discussed with reference to FIG. 5.

The first mechanical separation device 202 may include a single stage or multiple stages of separation in the device. For instance, there may be a two-stage washing in the first mechanical separation device 202 in an embodiment. However, any number of washings may be used, such as one, two, three, or four stages of washing. The washing of the fiber and/or large solids helps to wash the solubles, oil, starch, gluten or protein away from the fiber.

The ACT process 106 directs the large-suspended solids stream 204 to a second tank 210. The second tank 210 may be a cook tank or any type of tank that includes an agitator and heating or cooling capabilities by direct or indirect heat, a combination of the two, steam, heat exchangers, pressure, direct or indirect cooling mechanism, or the like.

The ACT process 106 adds water 212 to the second tank 210. For instance, the water 212 being added to the large-suspended solids stream 204 may create a dilute lower-solids concentration stream in the second tank 210. The water 212 may include but is not limited to, hot, warm, or cold dilution water, water that was used in a washing portion of the first mechanical separation device 202, or a combination of the dilution water and the water that was used in the washing portion of the first mechanical separation device 202. In an alternative embodiment, the water may be from water that is used in a washing portion of a second mechanical separation device. The water 212 may range from a temperature of about 0° C. to about 150° C. (about 32 to about 302° F., about 273 to about 423 K). The ACT process 106 mixes the water 212 and the large-suspended solids stream 204 together in the second tank 210 with the agitator.

In an embodiment, the ACT process cools or heats the second tank 210 to a temperature range of about 50° C. to about 150° C. (about 122° F. to about 302° F., about 323 to about 423 K) for an average residence time of about 30 minutes to about 4000 minutes. In an embodiment, the lower-solids stream created in the second tank 210 may be heated to about 82° C. (about 180° F., about 355 K)) for about 240 minutes. In other embodiments, the lower-solids stream created in the second tank 210 may be heated to less than about 82° C. (about 180° F., about 355 K) for about 120 minutes, and additional times of another 60 minutes, another 30 minutes, another 20 minutes, another 10 minutes, or another 5 minutes. The additional times may include one or multiple times combined and then added to the 120 minutes. The residence time and temperature may be predetermined based on variables. The variables may include size of the tank, amount of material in the tank, type of grain, and the like.

The cooling, heating, or incubation of the large-suspended solids stream 204 with the water 212 and any processing aids such as pH, enzymes, and the like cause the starch granules to absorb the water as heated. Thus, the water 212 is absorbed inside the granule. This swelling of the granule allows for improved enzyme action when returned to the start of the slurry process, the jet cook process, or the liquefaction process.

Next, the ACT process 106 sends the lower-solids stream 214 from the second tank 210 through a pump 216. In other embodiments, there may be additional tanks after the second tank 210. These additional tanks help with staging of the lower-solids stream 214. Staging may include providing constant controlled time in the tanks for each of the particles. The ACT process 106 can, as desired, send a portion of the lower-solids stream 214 back to the second tank 210 through the pump 216 and another portion of the lower-solids stream 214 (e.g., the large-size particles combined with water) to a second mechanical separation device 218.

The second mechanical separation device 218 further separates the solids from the liquids a second time. This basically separates the components in the lower-solids stream 214, which is composed of the large-suspended solids stream 204 and water 212. The second mechanical separation device 218 produces another liquids and fine-suspended solids stream 220 (i.e., second liquids and fine-suspended solids stream) and another large-suspended solids stream 222 (i.e., second large-suspended solids stream).

The ACT process 106 sends the another liquids and fine-suspended solids stream 220 back to the start of the process. For instance, the another liquids and fine-suspended solids stream 220 may be sent to the beginning of the slurry tank 104. In other embodiments, the another liquids and fine-suspended solids stream 220 may be sent to the jet cooker, the liquefaction tanks, or the like. This reuse removes the excess water from the slurry and/or the mash and fermentation processes.

The ACT process 106 further sends the another large-suspended solids stream 222 to the first tank 208, which may be a remix tank. Here, the ACT process 106 combines the another large-suspended solids stream 222 with the liquids and fine-suspended solids stream 206 in the first tank 208. The ACT process 106 may stir with an agitator in the first tank 208 to homogenize the combined streams of 222 and 206. Other homogenization methods that may be employed include but are not limited to a static mixer, a ribbon blender, a recirculation pump, and the like. The ACT process 106 further sends the combined stream 224 of the another large-suspended solids stream 222 with the liquids and fine-suspended solids stream 206 through a pump to the liquefaction tank 114 be fermented in the fermentation tank 116. In another embodiment, the combined stream 224 may be sent to be cooked by a jet cooker or additional liquefaction holding tank and moved to subsequent tank(s).

The second mechanical separation device 218 includes at least one of a paddle machine, a washing paddle machine, a filtration centrifuge, a pressure screen, a gravity DSM screen, a vibration screen, and the like to separate the solids from the liquids. In an embodiment, the second mechanical separation device 218 is a paddle machine having at least four rotating paddles with a stationary drum and an outer wall configured as a screen. In other embodiments, the paddle machine may include at least one rotating paddle or more, up to 20 rotating paddles. In embodiments, the second mechanical separation device may have a single stage of washing or multiple stages of washing.

There may be many combinations of mechanical separation devices. The mechanical separation devices may include but is not limited to, from one to ten devices. In embodiments, the first mechanical separation device 202 and the second mechanical separation device 218 may be the same type of device or each may be separate types of devices. For instance, in an embodiment, the first mechanical separation device 202 may be a paddle machine with two stages of washing and the second mechanical separation device 218 may be a paddle machine with a single stage of washing. There may be combinations of different or same types of first and second mechanical screening devices, different stages of washing in each mechanical screening devices, and a number of different mechanical screening devices.

In embodiments, the ACT process 106 may include multiple mechanical separation devices that are in sequential washing stages. For instance, the multiple mechanical separation devices may occur in series in which the water flows through the various mechanical separation devices. In another embodiment, the ACT process 106 may include the multiple mechanical separation devices occurring in parallel. The multiple mechanical separation devices occur in parallel for process flows that may be too large for one system.

This embodiment results in about 0% to about 6% increase yield in alcohol and about 0% to about 99% increase in oil recovered. The results are further discussed under the Examples of Test Results Section. The ACT process 106 does not increase solids content during the conversion of starch to alcohol. The increase in solids content negatively affects the viscosity of the material or the yield from a fermentation process. Furthermore, the ACT process 106 does not have significant energy penalties, does not include significant capital costs, and does not cause known degrading of the quality of the co-products, such as the DDGS.

Figure 3:
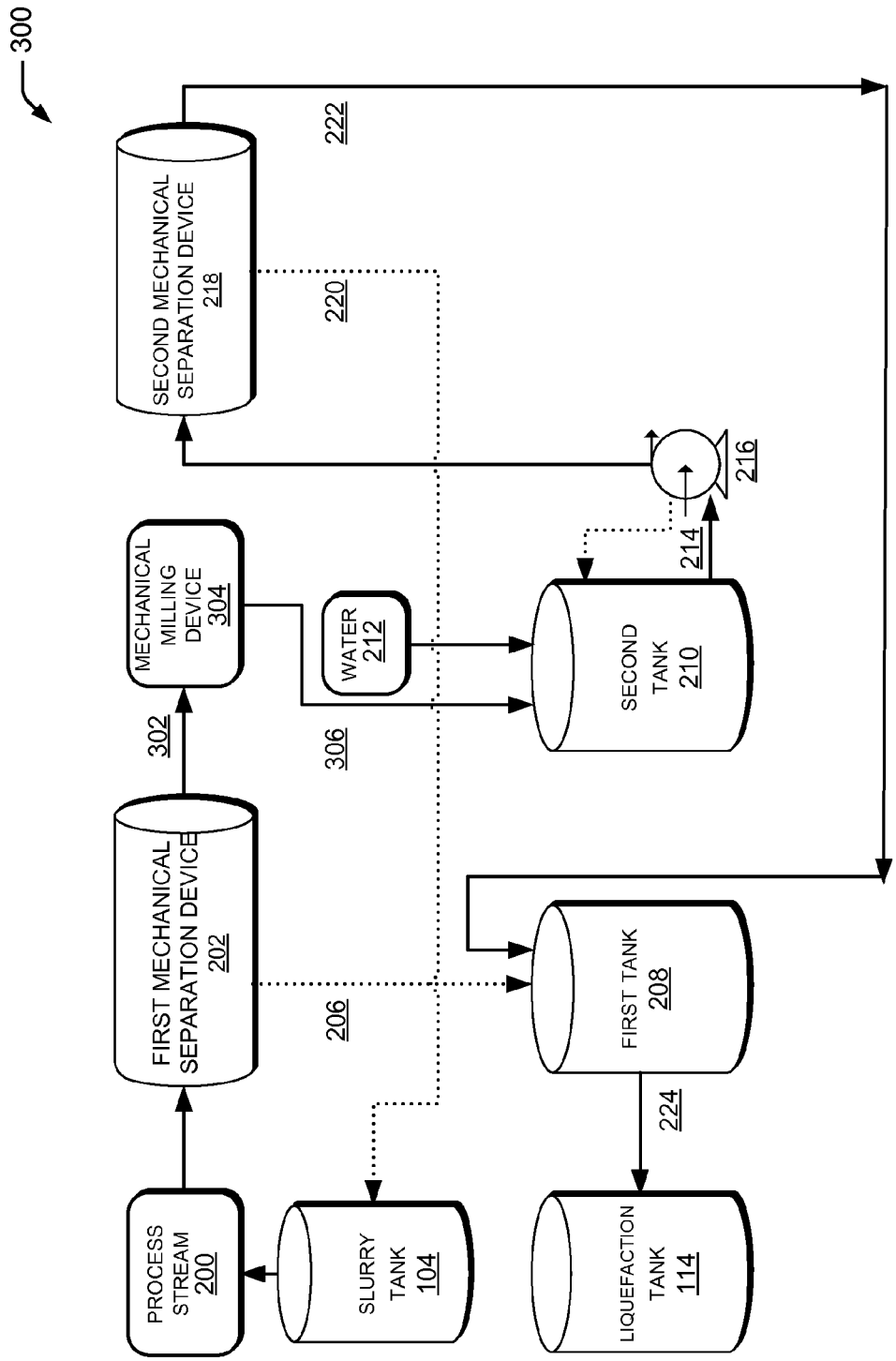
FIG. 3 illustrates another example embodiment of the ACT process with separation steps and a milling step.

FIG. 3 is similar to FIG. 2, except this figure illustrates another embodiment of the ACT process 300 with a mechanical milling device in the system. The process 300 includes the phases of initially separating the components of the feedstock in a process stream, milling the large-size particles from the separated streams, heating or cooling the large-size particles from the separated streams, and further separating the large-size particles for processing. Details of some of the phases will be discussed below with reference to FIG. 3.

In the initial separating phase, the process 300 uses a first mechanical separation device 202 to separate components of the feedstock in the process stream 200 to produce the liquids and fine-suspended solids stream 206 and the large-suspended solids stream 302.

In the milling phase, the process 300 sends the large-suspended solids stream 302 through the mechanical milling device 304. The mechanical milling device 304 may be a disc mill, a pin mill, a grind mill, a hammer mill, a roller mill, a colloidal mill, a collider mill or any type of shearing device, to reduce the size of the particles or to tear fragile materials, such as starch, protein, or germ, from tough materials, such as fiber. For instance, the mechanical milling device 304 may grind or macerate the large-sized particles or solids in the large suspended-solids stream 302 to reduce the size of the particles and to break down the bonds between the fiber/germ and the starch, the fiber/germ and the protein, and the fiber/germ and the oil. For instance, the process 300 reduces the amount of starch in the fiber/germ from about 6% to about 3%, reduces the amount of protein in the fiber/germ from about 29% to about 21%, and reduces the amount of oil in the fiber/germ from about 9% to about 6%.

The process 300 macerates the large-suspended solids stream 302 with high shear maceration. In an embodiment, a disc mill may include two plates with a grind pattern. For instance, one plate may spin while the other plate is stationary. In another embodiment, the disc mill may include two plates that may spin in opposite directions. The variables for the disc mill include a rotation rate of the plate and an adjustment gap between the plates. A higher rotation and/or a smaller gap between the plates may provide better performance in shearing the large-suspended particles. The size of the particles may range from about 0 to about 2000 microns, more likely about 100 to about 800 microns.

The process 300 sends the ground large particles 306 from the large-suspended solids stream 302 to the second tank 210. This embodiment results in about 0.5% to about 3% increase yield in alcohol and about 62% to about 123% increase in oil recovered. The results are further discussed under the Examples of Test Results Section. The rest of the process 300 is similar to the ACT process 106 discussed with reference to FIG. 2.

In an alternative embodiment, the process 300 may split the large-suspended solids stream 302 by sending a first portion directly to the second tank 210 and a second portion to the mechanical milling device 304. These first and second portions may be in different percentages, such as but are not limited to, 30-70%, 40-60%, 60-40%, and the like, respectively. The rest of the process 300 is similar to the ACT process 106 discussed with reference to FIG. 2.

The goal is to make the starch and oil inside the germ more accessible through shearing of the large-size particles. The mechanical milling device uses mechanical energy to free the starch by maceration, to break up protein-starch interactions, and to condition the germ for better oil leach properties. Thus, more starch is available for fermentation and more oil is available for recovery. The mechanical milling device has shown to provide lower residual starch in spent grains. For instance, the example results indicate a reduction of about 20 to 50% in residual starch, which helps increase the amount of alcohol produced per bushel.

Figure 4:
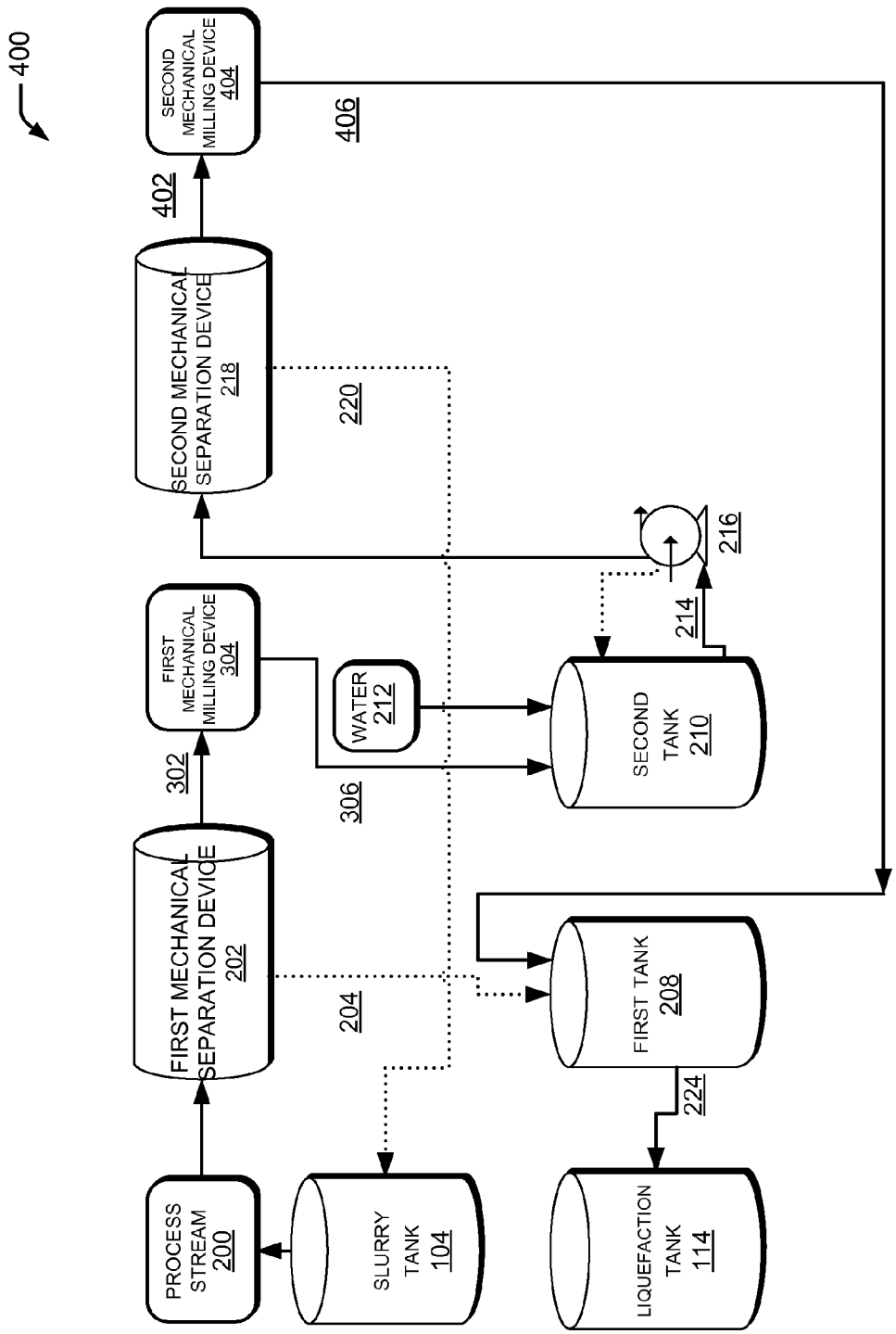
FIG. 4 illustrates another example embodiment of the ACT process with separation steps and milling steps.

FIG. 4 is similar to FIG. 3, except this figure illustrates another embodiment of the ACT process 400 with two mechanical milling devices in the process. The mechanical milling device 304 described with reference to FIG. 3 is now referred to as a first mechanical milling device.

In the second milling phase, the process 400 sends another large-suspended solids stream 402 through a second mechanical milling device 404. The second mechanical milling device 404 may be a disc mill, a pin mill, a grind mill, a hammer mill, a roller mill, or any type of shearing device, to reduce the size of the particles or to tear fragile materials, such as starch, protein, or germ, from tough materials, such as fiber. For instance, the second mechanical milling device 404 may grind or macerate the large-sized particles or solids in the large suspended-solids stream 402 to further reduce the size of the particles and to further break down the bonds between the fiber/germ and the starch, the fiber/germ and the protein, and the fiber/germ and the oil. For instance, the process 400 reduces the amount of starch in the fiber/germ from about 6% to about 2%, reduces the amount of protein in the fiber/germ from about 29% to about 23%, and reduces the amount of oil in the fiber/germ from about 9% to about 4%. The process 400 sends the ground large-suspended solids stream 406 to to the first tank 208.

Figure 5:
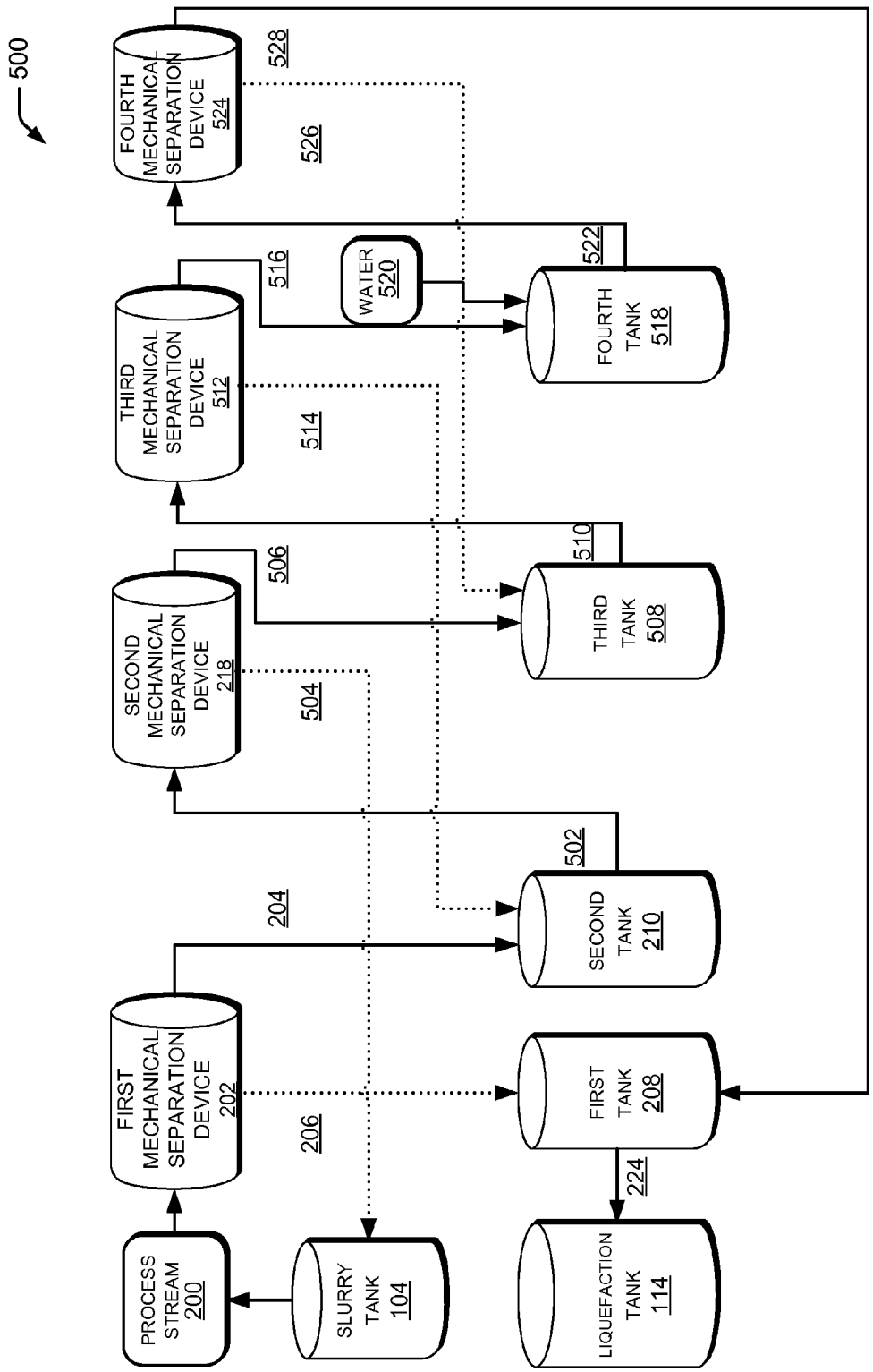
FIG. 5 illustrates another example embodiment of the ACT process with separation steps using a counter-flow wash process.

FIG. 5 is similar to FIG. 2, except this figure illustrates another embodiment of the ACT process 500 with a counter-flow wash. The process 500 receives a process stream 200, which may be a slurry from a slurry tank 104 prior to being cooked. The process 500 separates the components, and further washes the material. The process 500 sends the process stream 200 through a first mechanical separation device 202, which separates components such as the larger solid particles 204 from the smaller particles and liquids stream 206 a first time. This is also referred to as a first pass.

The process 500 directs the liquids and fine suspended particles stream 206 to the first tank 208 and sends the large suspended solids stream 204 to the second tank 210. The first tank 208 may contain about 18% solids content. The first tank 208 receives another large suspended solids stream 528 from a fourth mechanical separation device 524.

Here, the combined streams 502 are mixed and heated to about 76° C. to about 85° C. (170° F. to about 185° F., about 349K to about 358K) for about 1 to about 60 minutes in the second tank 210. In an embodiment, the combined streams are mixed and heated to about 82° C. (about 180° F., about 355 K) for about 5 minutes. The process 500 sends this combined stream 502 from the second tank 210 to a second mechanical separation device 218.

The process 500 sends the combined stream 502 through the second mechanical separation device 218, which separates components such as the larger solid particles 506 from the smaller particles and liquids stream 504 a second time. This is also referred to as a second pass. The second mechanical separation device 218 washes and removes the starch from the fiber, producing another liquids and fine suspended particles stream 504 to be sent to the slurry tank 104, and another large suspended solids stream 506 to be sent to a third tank 508.

The process 500 sends the combined stream 510 from the third tank 508 through a third mechanical separation device 512, which separates components such as the larger solid particles from the smaller particles and liquids stream a third, or referred to as a third pass. The fourth tank 518 may contain about 7 to 10% solids content. The fourth tank 518 receives cook water 520. The cook water 520 may include but is not limited to hot dilution water. The cook water 520 may range from a temperature of about 75° C. to about 99° C. (about 348 K to about 372 K).

Here, the combined stream 522 is mixed and heated to about 76° C. to about 85° C. (170° F. to about 185° F., about 349 K to about 358 K) for about 1 to about 60 minutes. In an embodiment, the combined stream 522 is mixed and heated to about 82° C. (about 180° F., about 358K) for about 5 minutes. The process 500 further sends this combined stream 522 from the fourth tank 518 to a fourth mechanical separation device 524.

The fourth mechanical separation device 524 removes starch left on the fiber, producing another liquids and fine suspended particles stream 526 to be sent to the third tank 508 and another large suspended solids stream 528 to be sent to the first tank 208. The fourth mechanical separation device 524 separates components such as the larger solid particles from the smaller particles and liquids stream a fourth, or referred to as a fourth pass.

In an embodiment, the ACT process uses a mechanical separation step with two mechanical separation devices to separate a large suspended solids stream from a liquid with fine suspended solids. In other embodiments, the ACT process uses a series of two or more mechanical separation steps with a series of mechanical separation devices. In another embodiment, the ACT process uses a series of four mechanical separation steps. In another embodiment, the ACT process adds clean water to each stage of the concurrent washing in the series. In another embodiment, the ACT process adds water to each stage of the counter-flow washing in the series. This raises water activity for better starch to sugar conversion. Raising the water activity also increases oil leaching rate and oil leaching completeness from germ moieties.

Figure 6:
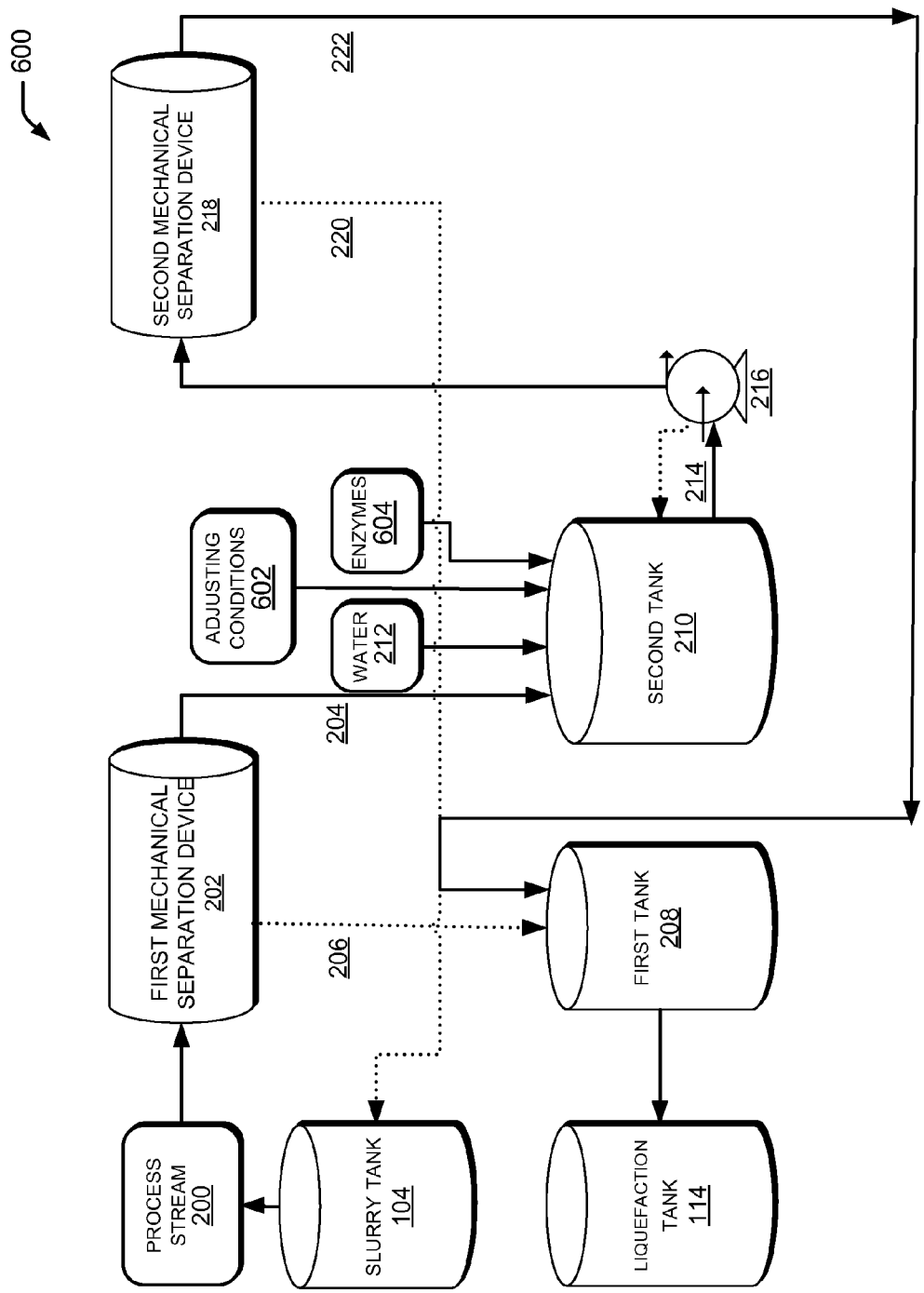
FIG. 6 illustrates another example embodiment of the ACT process with the addition of enzymes.

FIG. 6 is similar to FIG. 2, except this figure illustrates another embodiment of the ACT process 600 by adjusting conditions and adding enzymes in the system. The process 600 includes the phases of initially separating the components in a process stream, adjusting variables by treating or applying mechanical means to the large-particles stream, adding enzymes to the large-particles stream, and further separating the large-particles stream for processing. Details of the phases that are not similar to FIG. 2 will be discussed below with reference to FIG. 6.

In the adjusting conditions 602 phase, the process 600 adjusts temperature, pH, or processing aids to desired conditions and holds the lower-solids stream for a predetermined amount of time in the second tank 210. The process 600 may perform a single function or a combination of these functions, such as add water 212 to the large-size particles stream, add heat or cool the large-size particles stream, and adjust the pH or other processing aids in the second tank 210.

As an example, the process 600 may add water 212 to cool or to heat the large-particles stream. For instance, the process 600 may adjust the temperature from about 40.6° C. to about 96.1° C. (about 105° F. to about 205° F.) in the second tank 210. As another example, the process 600 may adjust the pH by adding base or acid to the large-particles stream in the second tank 210. For instance, the process 600 may add sodium hydroxide, phosphoric acid, sulfuric acid, sulfur dioxide, sodium bisulfate, ammonium bisulfate, and the like.

In the enzyme addition phase, the process 400 adds enzymes 604, such as alpha-amylase, proteases, pullulanases, or other hydrolytic enzymes, as desired, to the large-size particles that have been heated or cooled along with pH, temperature, or other processing aids adjusted in the second tank 210. This adding enzymes 604 phase increases the conversion of starch to dextrins, and other long-chain molecules to smaller-chain molecules, which further improves yield of product. The removal of the liquid and fine-suspended particles stream 206 allows a longer residence time for a fixed tank space for incubation of the large-size particles. The longer residence time in the second tank 210 combined with the lower suspended materials completes the starch to dextrin process more completely. Also, the additional enzymes 604 being added to the lower-solids stream may cause additional oil to leach from fine germ particles. The rest of the process 600 is similar to the ACT process 106 discussed with reference to FIG. 2.

In another embodiment, the process may include adjusting the variables and incubating the large-particles stream without adding enzymes. The phases may include initially separating the components in a process stream, adjusting conditions such as temperature by heating or cooling the large-size particles from the separated streams, or adjusting pH or the processing aids to the large-particles stream, and further separating the large-particles stream for processing.

In yet other embodiments, the process may include a third tank to further adjust the variables, with and without adding enzymes in the second tank. For instance, the phases may include initially separating the components in a process stream, adjusting conditions such as temperature by heating or cooling the large-size particles or adjusting pH or the processing aids to the large-particles stream, adding enzymes which is optional, sending the material to a third tank to further adjust variables such as temperature by heating or cooling the large-size particles or adjusting pH or the processing aids to the large-particles stream, and further separating the large-particles stream for processing.

Figure 7:
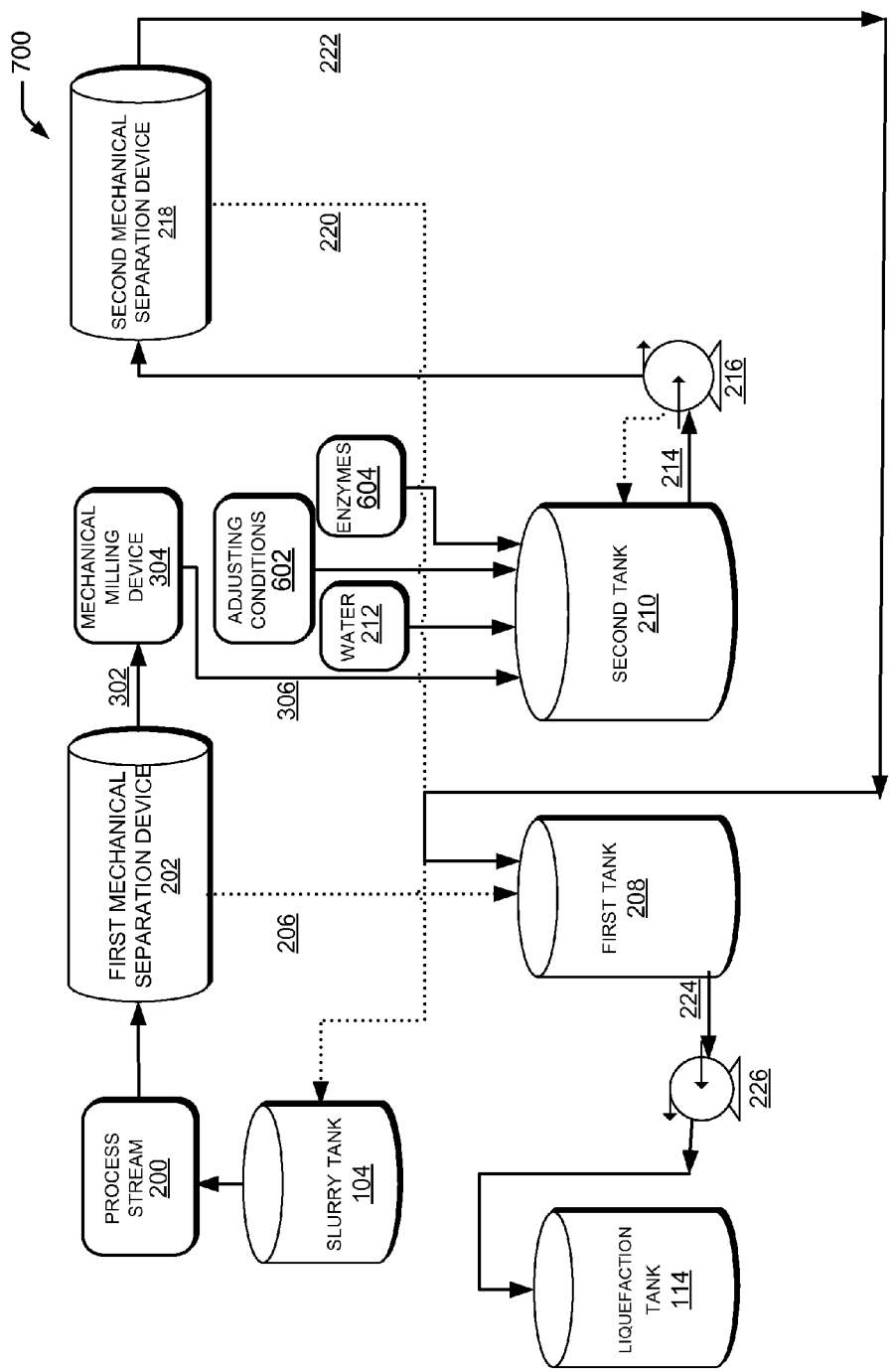
FIG. 7 illustrates another example embodiment of the ACT process with the milling step and with the addition of enzymes.

FIG. 7 is similar to FIG. 2, except this figure illustrates another embodiment of the ACT process 700 with a mechanical milling device, adjusting conditions and adding enzymes in the system. The process 700 includes the phases of initially separating the components of the feedstock in a process stream, milling the large-size particles from the separated streams, adjusting conditions to the large-particles stream in the tank, adding enzymes in the tank, and further separating the large-size particles for processing. Details of the phases will be discussed below with reference to FIG. 7.

In the initial separating phase, the process 700 uses a first mechanical separation device 202 to separate components of the feedstock in the process stream 200 to produce the liquids and fine-suspended solids stream 206 and the large-suspended solids stream 302.

In the milling phase, the process 700 sends the large-suspended solids stream 302 through the mechanical milling device 304. The mechanical milling device 304 may be a disc mill, a pin mill, a grind mill, a hammer mill, a roller mill, a colloid mill or any type of shearing device, to reduce the size of the particles. For instance, the mechanical milling device 304 may grind the large-sized particles or solids in the large suspended-solids stream 302 to reduce the size of the particles and to break down the bonds between the fiber/germ and the starch, the fiber/germ and the protein, and the fiber/germ and the oil. For instance, the process 700 reduces the amount of starch in the fiber/germ from about 6% to about 3%, reduces the amount of protein in the fiber/germ from about 29% to about 21%, and reduces the amount of oil in the fiber/germ from about 9% to about 6%.

The process 700 macerates the large-suspended solids stream 302 with high shear maceration. In an embodiment, a disc mill may include two plates with a grind pattern. In an embodiment, the two plates may be spinning in opposite directions. In another embodiment, one plate may spin while the other plate is stationary. The variables for the disc mill include a rotation rate of the plate and an adjustment gap between the plates. A higher rotation and/or a smaller gap between the plates may provide better performance in shearing the large-suspended particles. The size of the particles may range from about 0 to about 2000 microns, more likely to be about 100 to about 800 microns. The process 700 sends the ground large particles 306 from the large-suspended solids stream 302 to the second tank 210.

In the adjusting conditions 602 phase, the process 700 adjusts temperature, pH, or processing aids to desired conditions and holds the lower-solids stream for a predetermined amount of time in the second tank 210. The process 700 may perform a single function or a combination of these functions, such as add water 212 to the large-size particles stream, add heat or cool the large-size particles stream, and adjust the pH or other processing aids in the second tank 210.

As an example, the process 700 may add water 212 to cool or to heat the large-particles stream. For instance, the process 700 may adjust the temperature from about 40.6° C. to about 96.1° C. (about 105° F. to about 205° F.) in the second tank 210. As an example, the process 700 may adjust the pH by adding base or acid to the large-particles stream in the second tank. For instance, the process 700 may add sodium hydroxide and the like. Furthermore, the process 700 may incubate the large-particles stream for additional residence time as described previously.

In the enzyme addition phase, the process 700 adds enzymes 604, such as alpha-amylase or other hydrolytic enzymes, as desired, to the large-size particles after being heated or cooled, and/or pH adjusted in the second tank 210. This enzyme addition phase increases the conversion of starch to dextrins, which further improves yield of product. The removal of the liquids and fine-suspended solids stream 206 allows for a longer residence time for a fixed tank space for incubation of the large-size particles. The longer residence time in the second tank 210 combined with the lower suspended materials complete the starch to dextrin process more completely. Also, the enzymes being added to the lower solids may cause oil to leach from fine germ particles. The rest of the process 700 is similar to the ACT process 106 discussed with reference to FIG. 2.

Figure 8:
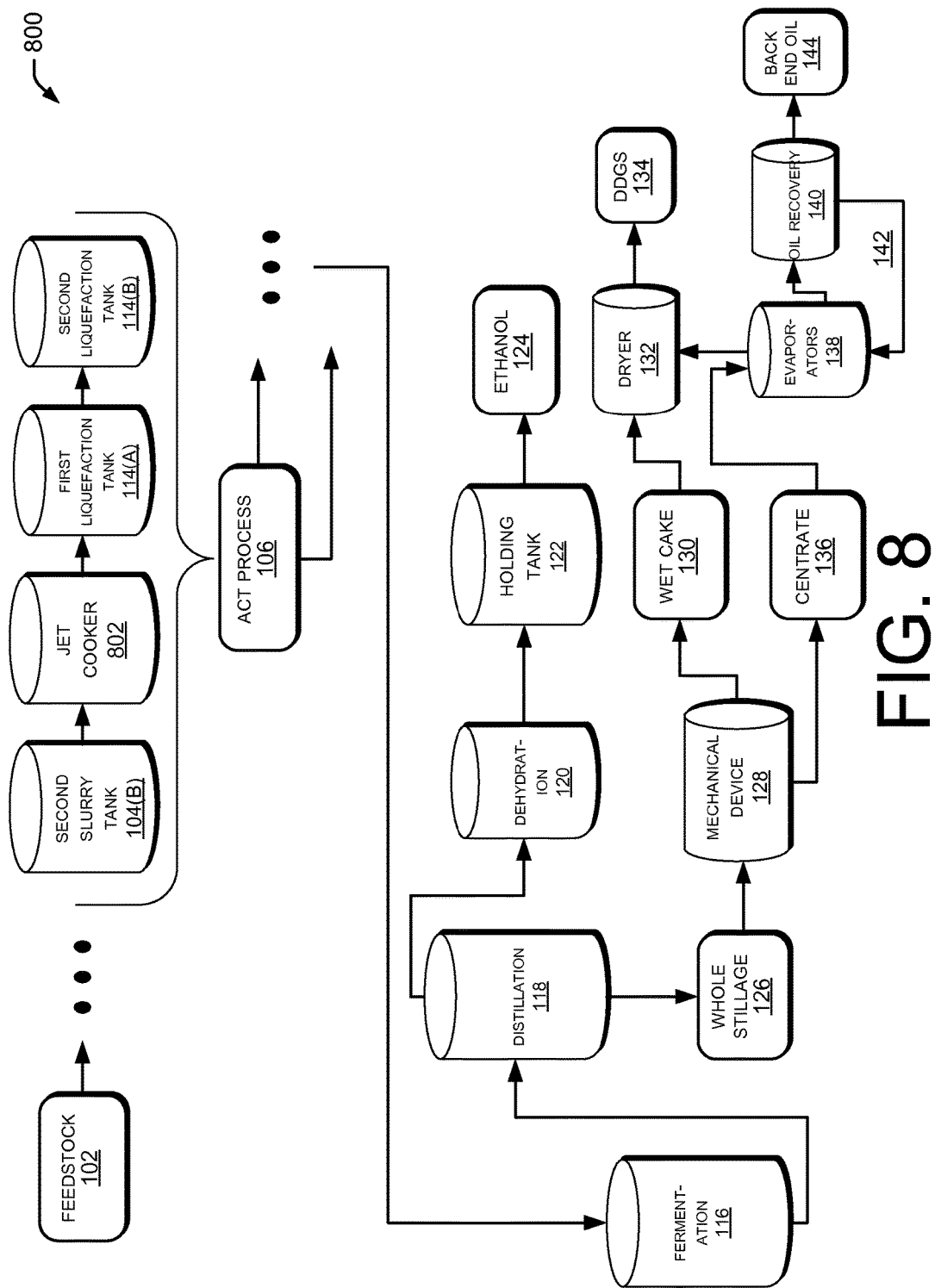
FIG. 8 illustrates another example environment for treating the large-size particles obtained from a process stream in the ACT process.

FIG. 8 illustrates another example process 800 for treating suspended solids obtained from different tanks. This process 800 is similar to the process in FIG. 1. However, the process 100 in FIG. 1 obtains the process stream from a first slurry tank. Here, the process 800 stream obtains the process stream from any of the following, the second slurry tank 104(B), the jet cooker 602, the first liquefaction tank 114(A), or the second liquefaction tank 114(B) for illustrative purposes.

Examples of Test Results

The ACT process was replicated in a laboratory setting using the different embodiments described above. Tables I. and II. illustrate results of Ethanol Yield and Liberation of Oil, respectively.

Table I. below indicates the different variables for embodiments used in the experiments for Ethanol Yield.

TABLE I

Ethanol Yield

| Samples | % Weight Loss - Solids Leveled Ferm Hours 70 | EtOH Yield (% of Control) |
|---|---|---|
| Dil L2 | 11.22 | Control |
| 4 Hr Cook | 11.87 | 105.8 |
| Short Grind + 4 Hr | 11.31 | 100.8 |
| Long Grind + 4 Hr | 11.61 | 103.4 |
| Jet Cook + 4 Hr | 11.67 | 103.9 |
| 4 Hr @ 95° C. | 11.70 | 104.3 |

Table I shows in a first vertical column the different samples tested and shows in a first row, Samples, % Weight Loss—Solids "Leveled" and EtOH Yield, which is a percent of the control. Table I. further shows in the second row, Ferm Hours for the number of hours of fermentation, such as 70 hours for each of the samples and (% of the Control).

Table I. illustrates a control is referenced as "Dil L2." This is a sample pulled from a commercial facility as normally processed by the facility and represents the control scenario.

A first sample, is referenced as "4 Hr Cook." This sample included an advanced cook time of about four hours at 85° C. in a cook tank. The yield is 105.8% of the control.

A second sample, referenced as "Short Grind+4 Hr" included the ACT process with a cook time of about four hours at about 85° C. and a short amount of grinding time in the disc mill. For instance, the short grinding time ranged from about 20 seconds to about 30 seconds. This yield was 100.8% of the control.

A third sample referenced as "Long Grind+4 Hr" included the advanced cook time of about four hours at about 85° C. and a long amount of grinding time in the disc mill. For instance, the long grinding time ranged from about 1.8 minutes to about 2.2 minutes. This yield was 103.4% of the control.

A fourth sample referenced as "Jet Cook+4 hr" included the advanced cook time of about four hours at 85° C. combined with using the jet cooker at 130° C. As indicated, the yield is 103.9% of the control.

A fifth sample referenced as "4 Hr @ 95 C Cook" included the advanced cook time of about four hours at 95° C. As indicated, the yield is 104.3% of the control.

In summary, these results indicate the ACT process produces about 1 to about 5% higher ethanol yield compared to the control. Thus, there are many opportunities to increase the ethanol yield by using the various embodiments of the ACT process.

Table II. below indicates the amount of oil liberated during the ACT process.

TABLE II

Free Oil (emulsified and unemulsified) from Post Liquefaction

| Samples (Free oil + Emulsified Oil) | % Oil per Dry Solids | Delta to Control (%) | Dry Solids in Samples |
|---|---|---|---|
| LLF L2 Mash | 0.52 | 100 | 31.7 |
| Low Density L2 Mash | 0.60 | 100 | 24.6 |
| No Grind 4 Hr Cook | 1.20 | 199 | 24.2 |
| Short Grind 4 Hr Cook | 0.98 | 162 | 22.7 |
| Long Grind 4 Hr Cook | 1.34 | 223 | 24.7 |
| Long Grind + Jet + 4 Hr | 1.28 | 212 | 24.6 |
| Long Grind + 95° C. 4 Hr | 1.46 | 242 | 24.8 |

Note
solids content per sample type

Table II. shows in a first vertical column the different samples tested and shows in a first row, % Oil per Dry Solids, Delta to Control (%), and Dry Solids in Samples.

The control is referenced as "LLF L2 Mash." This indicates the sample was retrieved from a second liquefaction tank.

The first sample is referenced as "Low Density L2 Mash." This first sample did not include any grinding using the milling device, and is used as a secondary control to LLF L2 Mash. This sample was created by adding water to the LLF L2 sample.

The second sample is referenced as "No Grind 4 Hr Cook." The second sample also did not include any grinding with the milling device, but was cooked in the ACT process at about 85° C. for about four hours. The second sample shows an increase of 99% in liberating the oil compared to the control.

The third sample is referenced as "Short Grind 4 Hr Cook." The third sample included a short grinding time of about 20 seconds to 30 seconds using the milling device, and cooked in the ACT process at about 85° C. for about four hours. The third sample shows an increase of 60% in liberating the oil compared to the control.

The fourth sample is referenced as "Long grind 4 Hr Cook." The fourth sample included a long grinding time of about 1.8 minutes to about 2.2 minutes using the milling device, and cooked in the ACT process at about 85° C. for about four hours. The fourth sample shows an increase of 123% in liberating the oil compared to the control.

The fifth sample is referenced as "Long Grind Jet 4 Hr." The fifth sample included a long grinding time of about 1.8 minutes to about 2.2 minutes using the milling device, cooked in the ACT process at about 85° C. for about four hours, and combined with the jet cook at about 130° C. for about 30 minutes. The fifth sample shows an increase of 112% in liberating the oil compared to the control.

The sixth sample is referenced as "Long Grind+95 C+4 Hr." The sixth sample included a long grinding time of about 1.8 minutes to about 2.2 minutes using the milling device and cooked in the ACT process at about 95° C. for about four hours. The sixth sample shows an increase of 142% in liberating the oil compared to the control.

Overall, the results indicate an increase ranging from 60 to 142% in liberating the oil compared to the control. Thus, there are many opportunities to increase the amount of oil that is liberated with the ACT process.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed is:

1. A method used in an alcohol production facility, the method comprising:
   separating a first suspended-solids stream from a first liquid stream containing fine-suspended solids of a process stream by using a first separation device in a counter-flow wash process;
   sending the first liquid stream containing fine-suspended solids to a first tank;
   milling a portion of the first suspended-solids stream by using a mechanical milling device;
   adding water to the milled particles stream to create a lower-solids stream in a second tank;
   heating the lower-solids stream in the second tank at a temperature less than about 95° C.; and
   further separating a second suspended-solids stream from a second liquid stream containing fine-suspended solids of the lower-solids stream by using a second separation device in the counter-flow wash process; and
   combining the second suspended-solids stream with the first liquid stream containing fine-suspended solids and mixing to homogenize;
   wherein the method is performed downstream of slurry and upstream of fermentation.

2. The method of claim 1, wherein the heating of the lower-solids stream in the second tank has an average residence time from about 20 minutes to about 300 minutes.

3. The method of claim 1, wherein the mechanical milling device comprises at least one of a disc mill, a pin mill, a grind mill, a hammer mill, or a roller mill.

4. The method of claim 1, further comprising:
   sending a first portion of the second suspended-solids stream from the second mechanical separation device to a tank; and
   milling a second portion of the second suspended-solids stream by using another mechanical milling device.

5. The method of claim 1, wherein the lower-solids stream in the second tank is heated to a temperature lower than about 80° C.(about 353 K) to remove starch.

6. The method of claim 1, wherein the separating, the milling, and the heating will cause an increase in ethanol yield that ranges from about 1% to about 3%.

7. The method of claim 1, wherein the process stream comprises being obtained as slurry from a slurry tank prior to being cooked or as mash from a liquefaction tank after being cooked.

8. The method of claim 1, wherein the first separation device or the second separation device comprises at least one of a paddle machine, a washing paddle machine, a filtration centrifuge, a pressure screen, a vibration screen, or a gravity screen.

9. The method of claim 1, wherein the adding water to the milled particles stream comprises water that is at least one of dilution water, water used in a washing portion of the first separation device, or a combination of the dilution water and the water used in the washing portion of the first separation device.

* * * * *